United States Patent
Beier et al.

(10) Patent No.: US 10,292,949 B2
(45) Date of Patent: May 21, 2019

(54) PHARMACEUTICAL COMPOSITION COMPRISING RIMEPORIDE FOR TREATING DISEASES ASSOCIATED WITH INSULIN RESISTANCE AND β-CELL DYSFUNCTION

(71) Applicant: Merck Patent GmbH, Darmstadt (DE)

(72) Inventors: Norbert Beier, Reinheim (DE); Wolfgang Scholz, Eschborn (DE); Ulrich Betz, Reinheim (DE); Marian Braendle, Starzach (DE)

(73) Assignee: Meck Patent GmbH, Darmstadt (DE)

( * ) Notice: Subject to any disclaimer, the term of this patent is extended or adjusted under 35 U.S.C. 154(b) by 0 days.

(21) Appl. No.: 15/468,295

(22) Filed: Mar. 24, 2017

(65) Prior Publication Data

US 2017/0189354 A1    Jul. 6, 2017

Related U.S. Application Data

(63) Continuation of application No. 12/991,524, filed as application No. PCT/EP2009/002701 on Apr. 11, 2009.

(30) Foreign Application Priority Data

May 9, 2008   (EP) .................................... 08008763

(51) Int. Cl.
  *A61K 31/155*   (2006.01)
  *A61K 9/00*    (2006.01)

(52) U.S. Cl.
  CPC .......... *A61K 31/155* (2013.01); *A61K 9/0053* (2013.01)

(58) Field of Classification Search
  CPC .............................. A61K 31/155; A61K 9/0053
  See application file for complete search history.

(56) References Cited

U.S. PATENT DOCUMENTS

| | | | |
|---|---|---|---|
| 5,627,193 A | 5/1997 | Fujiwara | |
| 5,637,691 A | 6/1997 | Frye | |
| 5,744,641 A | 4/1998 | Gericke et al. | |
| 6,673,968 B1 | 1/2004 | Gericke et al. | |
| 6,706,921 B2 | 3/2004 | Bartmann | |
| 6,770,678 B1 | 8/2004 | Kurz | |
| 7,179,830 B2 | 2/2007 | Lang | |
| 7,875,625 B2 | 1/2011 | Uemoto | |
| 8,067,614 B2 | 11/2011 | Heinelt | |
| 2003/0212104 A1 | 11/2003 | Tracey et al. | |

FOREIGN PATENT DOCUMENTS

| | | |
|---|---|---|
| DE | 199 03 275 A1 | 8/2000 |
| DE | 199 51 418 A1 | 5/2001 |
| DE | 103 05 070 A1 | 8/2004 |
| EP | 0 758 644 A1 | 2/1997 |
| EP | 1282598 B1 | 10/2004 |
| JP | 08-277269 A | 10/1996 |
| JP | 2007-314577 A | 12/2007 |
| WO | 2004069811 A1 | 8/2004 |
| WO | 2005026173 A1 | 3/2005 |
| WO | 2006088080 A1 | 8/2006 |

OTHER PUBLICATIONS

International Search Report of PCT/EP2009/002701 (dated Jun. 24, 2009).
J. C. Russell et al., "Insulin-Sensitizing and Cardiovascular Effects of the Sodium-Hydrogen Exchange Inhibitor, Cariporide, in the JCR," J. Cardiovasc. Pharmacol., vol. 46, No. 6 (Dec. 2005) pp. 746-753.
A. Semplicini et al., "Interactions Between Insulin and Sodium Homeostasis in Essential Hypertension," The American Journal of the Medical Sciences, vol. 307, Supp. 1 (Feb. 1994) pp. S43-S46.
M. Canessa et al., "Red Blood Cell Sodium-Proton Exchange in Hypertensive Blacks With Insulin-Resistant Glucose Disposal," Hypertension, vol. 22, No. 2 (Aug. 1993) pp. 204-213.
Patti et al. PNAS 100(14), 2003, 8466-8471.
Siffert et al. Basic Res Cardiol 91, 1996, 179-190.
Davies et al., "Intracellular pH and Na+/H+ antiport activity of cultured skin fibroblasts from diabetics," Kidney International, vol. 42 (1992), pp. 1184-1190.
Defronzo, Ralph A., "From the Triumvirate to the Ominous Octet: A New Paradigm for the Treatment of Type 2 Diabetes Mellitus," Diabetes, vol. 68, Apr. 2009, pp. 773-795.
Seino et al., "Report of the Committee on the Classification and Diagnostic Criteria of Diabetes Mellitus", Journal of Diabetes Investigation, vol. 1, Issue 5 Oct. 2010, pp. 212-228.
Toda et al., "Potent and Orally Bioavailable GPR142 Agonists as Novel Insulin Secretagogues for the Treatment of Type 2 Diabetes," ACS Medicinal Chemistry Letters, 2013, vol. 4, pp. 790-794.
Trevisan et al., "Na+/H+ Antiport Activity and Cell Growth in Cultured Skin Fibroblasts of IDDM Patients With Nephropathy," Diabetes, vol. 41, Oct. 1992, pp. 1239-1246.
English machine translation of DE10305070A1 published Aug. 26, 2004 to Beier Norbert Dr. of Merck Patent Gmbh.
Xu et al. Diabetes Dec. 1999; 48(12): 2270-2276.
Defronzo et al. Diabetes Care May 2005; 28(5): 1092-1100.

(Continued)

*Primary Examiner* — Sarah Pihonak
*Assistant Examiner* — Jason Deck
(74) *Attorney, Agent, or Firm* — Millen White Zelano and Branigan, PC; John Sopp

(57) ABSTRACT

The invention relates to a pharmaceutical composition comprising as active ingredient an effective amount of 2-Methyl-4,5-di-(methylsulfonyl)-benzoyl-guanidine, or derivatives thereof, for the prophylaxis and therapy of Type II diabetes mellitus, the Metabolic syndrome, diabetic nephropathy and/or neuropathy. Another object of the invention concerns the use of 2-Methyl-4,5-di-(methylsulfonyl)-benzoyl-guanidine, or derivatives thereof, for the enhancement of insulin sensitivity and the preservation or increase of ß-cell compensation.

13 Claims, 10 Drawing Sheets

(56) References Cited

OTHER PUBLICATIONS

Mu et al. Diabetes. Jun. 2006;55(6):1695-704.
Beysen et al. Diabetes Care May 2007; 30(5): 1143-1149.
Sm Turner et al. Curr Opin Drug Discov Devel 8 (1), 115-126. 1 2005 (Abstract).
Yoshida et al. International Journal of Pharmaceutics vol. 115, Issue 1, Feb. 28, 1995, pp. 61-67.
Peterson et al. Diabetes Treatment Guide. vol. 9 issue 5 downloaded from http://www.diabetestreatmentguide.org/symptoms-of-late-stage-diabetes/ on Sep. 3, 2014.

PHARMACEUTICAL COMPOSITION COMPRISING RIMEPORIDE FOR TREATING DISEASES ASSOCIATED WITH INSULIN RESISTANCE AND β-CELL DYSFUNCTION

The invention relates to a pharmaceutical composition comprising as active ingredient an effective amount of 2-Methyl-4,5-di-(methylsulfonyl)-benzoyl-guanidine, or derivatives thereof, for the prophylaxis and therapy of Type II diabetes mellitus, the Metabolic syndrome, diabetic nephropathy and/or neuropathy. Another object of the invention concerns the use of 2-Methyl-4,5-di-(methylsulfonyl)-benzoyl-guanidine, or derivatives thereof, for the enhancement of insulin sensitivity and the preservation or increase of ß-cell compensation.

Metabolic diseases such as obesity, insulin resistance (IR) and dyslipidemia are emerging as dominant causes of morbidity and mortality worldwide. Especially over the last decades, IR has become a highly prevalent condition in the general public, with enormous consequences for the public health system. IR is defined as the reduced, non-adequate response of the body to the normal actions of insulin. IR is an important risk factor for the development of cardiovascular disease and Type II diabetes mellitus (T2DM). In addition, IR is associated with a variety of cardiovascular risk-factors (obesity, dyslipidemia, hypertension and blood clotting disturbances) that when exhibited collectively is referred to as the Metabolic syndrome or Syndrome X. Considerable evidence now exists that IR may be the unifying causal factor underlying the Metabolic Syndrome (Turner & Hellerstein (2005) Curr Opin Drug Discovery & Develop 8(1): 115-126).

Current therapeutic interventions aiming to directly improve the insulin responsiveness of the tissues apply thiazolidinediones (TZDs). However, while the TZDs have been shown to improve whole-body insulin sensitivity, they recently have become known to increase the risk of heart failure and cardiovascular complications. Therefore, alternatives for the treatment of IR are necessary in the fight against the growing epidemic of deranged metabolic diseases, with one of its features being IR.

In addition to IR, pancreatic β-cell dysfunction plays a pivotal role in the progression from the pre-diabetic to the diabetic state. The recent development of agents, such as exendin-4 (Xu et al. Diabetes (1999) 48(12): 2270-2276; DeFronzo et al. (2005) Diabetes Care 28(5): 1092-1100) or a sitagliptin analog (Mu et al. (2006) Diabetes 55(6): 1695-1704), that may stimulate β-cell regeneration and increase β-cell mass has focused further interest on β-cell mass as a therapeutic target in T2DM.

Therefore, the technical problem forming the basis of the present invention is to provide a pharmaceutical composition allowing an effective application in the prevention or therapy of diseases that are associated with insulin resistance and/or ß-cell dysfunction, especially such compositions that improve the therapeutic efficacy and minimize adverse effects.

The present invention solves this problem by providing a pharmaceutical composition comprising as active ingredient an effective amount of 2-Methyl-4,5-di-(methylsulfonyl)-benzoyl-guanidine, and/or a physiologically acceptable salt and/or solvate thereof, for the prophylactic or therapeutic treatment and/or monitoring of diseases that are associated with insulin resistance and/or ß-cell dysfunction.

It has been surprisingly demonstrated by the inventors that 2-Methyl-4,5-di-(methylsulfonyl)-benzoyl-guanidine and said derivatives can be applied as active ingredients in a pharmaceutical composition in order to tackle medical indications such as T2DM and diseases being linked thereof.

Before filing this application, it is only known from EP 0 758 644 B1 that sulfonylbenzoyl-guanidines are inhibitors of the cellular $Na^+/H^+$ antiporter, i.e. they inhibit the $Na^+/H^+$ exchange mechanism of the cells, thereby being good anti-arrhythmic agents, which are suitable, in particular, for the treatment of arrhythmia occurring as a consequence of oxygen deficiency. The substances exhibit a good cardioprotective action and are therefore suitable for the treatment of acute myocardial infarction, infarction prophylaxis, post-infarction treatment, chronic cardiac insufficiency and for the treatment of angina pectoris. They furthermore counter all pathological hypoxic and ischemic damage, enabling the illnesses caused primarily or secondarily thereby to be treated. Owing to the protective action of these substances in pathological hypoxic or ischemic situations, further applications arise in surgical interventions for protection of organs with temporarily reduced supply, in organ transplants for protection of the removed organs, in angioplastic vascular or cardiac interventions, in ischemia of the nervous system, in the therapy of shock states and for the prevention of essential hypertonia. In addition, the compounds are suitable for diagnostic use for the recognition of illnesses accompanied by increased activity of the $Na^+/H^+$ antiporter, for example in erythrocytes, thrombocytes or leukocytes. Prior art has additionally suggested to employ these substances as therapeutic agents in illnesses caused by cell proliferation, such as arteriosclerosis, diabetes and late complications of diabetes, tumor illnesses, fibrotic illnesses, in particular of the lungs, liver and kidneys, and organ hypertrophia and hyperplasia.

But now, the present invention reveals the increase in whole-body IR while ß-cell compensation is simultaneously preserved. These phenomena are stimulated by the impact of the compound 2-Methyl-4,5-di-(methylsulfonyl)-benzoyl-guanidine, which forms the basis of the inventive remedy for such specified clinical pictures as T2DM and the Metabolic syndrome.

The aforementioned compound exhibits very valuable pharmacological properties along with good tolerability. Weight gain, fasting or random blood glucose levels are not changed at any dose tested in clinical trials. In contrast, fasting insulin is decreased in comparison to the pre-treatment by 2-Methyl-4,5-di-(methylsulfonyl)-benzoyl-guanidine. The insulin area-under-the-curve (AUC) value is also decreased after an oral glucose load while the AUC response to the glucose load remains similarly at pre- and post-treatment. It is an unexpected finding, however, that the lower insulin levels do not arise from the age-related drop in ß-cell function, since the compound of the invention maintains or even increases ß-cell response. Accordingly, 2-Methyl-4,5-di-(methylsulfonyl)-benzoyl-guanidine significantly enhances the peripheral insulin sensitivity.

Said biological activities of the compound of the invention may be determined by techniques known to the skilled artisan. Suitable experimental animals are, for example, mice, rats, guinea-pigs, dogs, cats, apes or pigs. The gold standard for the in-vivo assessment of IR is the euglycemic-hyperinsulinemic glucose clamp. Other tools are the steady-state plasma glucose (SSPG) test or the frequently sampled intravenous glucose tolerance test. Available techniques for measuring pancreatic β-cell proliferation in-vivo include the [$^3$H]thymidine ($^3$HdT) or 5-bromodeoxyuridine (BrdU) approaches. Techniques that are suitable to determine changes in insulin sensitivity and ß-cell dynamics have to be sensitive, reproducible, operationally simple and relatively high-throughput.

As stated before, insulin resistance is an important risk factor for the development of type 2 diabetes mellitus and cardiovascular disease. The pathogenesis of type 2 diabetes involves not only insulin resistance, but also progressive pancreatic insufficiency. A reliable, easily performed quantitative test has been developed. By means of this deuterated-glucose disposal test ($^2$H-GDT) both dimensions of type 2 diabetes can be quantified.

The glycolytic disposal of a glucose load by peripheral tissues, such as skeletal muscle, depends upon a number of insulin-dependent steps, including the transport, phosphorylation and passage through enzymes of the glycolytic pathway. In addition, glucose effectiveness, actions of glucoses per se to both inhibit hepatic glucose production and accelerate its uptake into tissues, also contributes to disposal of an oral glucose load. The $^2$H-GDT measures the rate of uptake, phosphorylation and glycolytic metabolism of glucose and thus can be used to quantify both insulin resistance (IR) and the adequacy of pancreatic ß-cell compensation. The $^2$H-GDT consists of an oral deuterated-glucose challenge followed by the measurement of heavy water ($^2$H$_2$O) production and plasma insulin concentrations. Because H atoms are released into tissue water during the glycolytic metabolism of glucose, measurement of $^2$H$_2$O production represents the rate of whole-body glycolytic disposal of glucose. $^2$H$_2$O production corrected for ambient insulin concentrations (i.e. glycolytic metabolism per unit of insulin) reveals tissue insulin sensitivity. Pancreatic compensation when corrected for the glycemic excursion (to account for the contribution of glucose effectiveness), reveals the degree to which glycolytic metabolism (absolute $^2$H$_2$O production) is matched to insulin sensitivity. In insulin resistant states, the pancreatic compensation is incomplete and glucose tolerance is impaired.

In detail, the recently developed, deuterated glucose disposal test ($^2$H-DGT) involving stable isotope-mass spectrometric assessment of whole-body glycolysis allows the assessment of IR by measuring the $^2$H$_2$O-production per unit of plasma insulin*glucose, which is based on the rate of release of deuterium ($^2$H) from an (oral) load of the animal or individual with deuterated [6,6'-$^2$H$_2$]glucose and the determined plasma insulin concentrations (Turner & Hellerstein (2005) Curr Opin Drug Discovery & Develop 8(1): 115-126). In addition, the degree of pancreatic ß-cell compensation to IR can be assessed by measuring the absolute $^2$H$_2$O production achieved after the [6,6'-$^2$H$_2$]glucose load. Adequacy of pancreatic compensation can be assessed by distinguishing between the glycolytic disposal per unit of ambient insulin (reflecting insulin sensitivity) and the absolute rate of glucose utilization achieved (reflecting pancreatic compensation to IR).

The $^2$H-GDT is designed to adhere to the following principles: i) ambient glucose and insulin concentrations should reflect metabolic conditions physiologically relevant, ii) the test should measure insulin-mediated glucose utilization by tissues and reveal IR in established models, and iii) the method should reflect comparable metabolic conditions as other tests of IR that are proven to be predictive for cardiovascular outcomes and T2DM risk. Serum insulin concentrations in the "dynamic range" between basal and maximal glucose utilization conditions fulfill these criteria (Beysen et al. (2007) Diab Care 30:1143-1149). Furthermore, the $^2$H-GDT, which measures the whole-body glycolysis in animals or humans in a quantitative manner, strongly correlates with the euglycemic-hyperinsulinemic glucose clamp or SSPG tests. The utilization of said kinetic assay is consequently preferred in the scope of the invention in order to determine the in-vivo effect of an agent on insulin sensitivity as well as insulin compensatory responses, in particular at relatively high-throughput, and in many commonly used preclinical animal models. In addition, the $^2$H-GDT is completely translational into the clinical setting with a similar degree of simplicity and throughput.

The active ingredient of the pharmaceutical composition according to the invention is an effective amount of the compound 2-Methyl-4,5-di-(methylsulfonyl)-benzoyl-guanidine, or pharmaceutically usable derivatives thereof. Such derivatives can be solvates of the matching compounds, salts or pro-drugs, for instance. Preference is given to solvates and/or physiologically acceptable salts.

A "pharmaceutical composition" in the meaning of the invention is any agent in the field of medicine, which comprises one or more substances or preparations thereof and can be used in prophylaxis, therapy, follow-up or aftercare of patients who suffer from diseases, which are associated with insulin resistance and/or ß-cell dysfunction, in such a way that a pathogenic modification of their overall condition or of the condition of particular regions of the organism could establish at least temporarily.

The term "ß-cell dysfunction" relates to any malfunction in proliferation of ß-cells and/or their cellular metabolism, which results in a diminished viability and/or metabolic activity with the consequence of reduced ß-cell compensation and insulin levels. Such loss of ß-cell function may be e.g. either caused by age-related deterioration or developed in the progression to type II diabetes, but any other causes shall be not excluded. A clear linkage of ß-cell dysfunction and insulin resistance is preferred in the scope of the invention, so that the inventive pharmaceutical composition targets diseases associated with both, ß-cell dysfunction and insulin resistance, in particular.

The terms "effective amount" or "effective dose" or "dose" are interchangeably used herein and denote an amount of the pharmaceutical compound having a prophylactically or therapeutically relevant effect on a disease or pathological conditions. A prophylactic effect prevents the outbreak of a disease. A therapeutically relevant effect relieves to some extent one or more symptoms of a disease or returns to normality either partially or completely one or more physiological or biochemical parameters associated with or causative of the disease or pathological conditions. The respective dose or dosage range for administering the pharmaceutical composition according to the invention is sufficiently high in order to achieve the desired prophylactic or therapeutic effect of reducing symptoms of the aforementioned diseases, particularly T2DM and said other upcoming diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation.

The compound 2-Methyl-4,5-di-(methylsulfonyl)-benzoyl-guanidine, which is used in the inventive manner, and the starting materials for its preparation, respectively, are produced by methods known per se, as described in the literature (for example in standard works, such as Houben- Weyl, Methoden der organischen Chemie [Methods of Organic Chemistry], Georg-Thieme-Verlag, Stuttgart), i.e. under reaction conditions that are known and suitable for said reactions. Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

For example, a process for the preparation of alkylbenzoylguanidine derivatives is described in EP 0 758 644 B1. In addition, EP 1 282 598 B1 teaches a method for the production of sulfonylbenzoylguanidium salts, wherein the preparation is particularly preferred in respect of the compound N-(4,5-bis-methanesulfonyl-2-methylbenzoyl)guanidine hydrochloride. Another process for preparing N-(4,5-bis-methanesulfonyl-2-methylbenzoyl)guanidine hydrochloride and the hydrochloride hydrate is disclosed in DE 199 51 418 A1. The aforementioned three documents are incorporated as reference in the disclosure of the invention hereby.

"Solvates" are regarded as attachments of inert solvent molecules to the compound, which are formed by respective mutual forces of attraction. Preferably, solvates are mono hydrates, dehydrates or alcoholates.

The provision of a salt can be performed by converting an acid of the compound 2-Methyl-4,5-di-(methylsulfonyl)-benzoyl-guanidine into the associated acid-addition salt using a base, for example by the reaction of equivalent amounts of the acid and the base in an inert solvent, such as ethanol, followed by evaporative concentration. Particular suitable bases for this reaction are those giving physiologically acceptable salts. For instance, an acid of the aforementioned compound can be converted into the corresponding metal salt, particularly an alkali metal or alkaline earth metal salt, or into the corresponding ammonium salt, using a base, for example sodium hydroxide, potassium hydroxide, sodium carbonate or potassium carbonate. Suitable for this reaction are, in particular, also organic bases, which give physiologically acceptable salts, such as ethanolamine.

On the other hand, a base of the compound 2-Methyl-4,5-di-(methylsulfonyl)-benzoyl-guanidine can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable acids. For instance, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethyl acetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, far example picrates, can be used for the isolation and/or purification of the compound 2-Methyl-4,5-di-(methylsulfonyl)-benzoyl-guanidine.

Preferred derivatives are 2-Methyl-4,5-di-(methylsulfonyl)-benzoyl-guanidine salts selected from the group of hydrochloride, methanesulfonate, hemi-sulfate, hemi-fumerate and hemi-malate. In a more preferred embodiment of the invention, 2-Methyl-4,5-di-(methylsulfonyl)-benzoyl-guanidine hydrochloride represents the active ingredient of the pharmaceutical composition.

The pharmaceutical composition may also comprise mixtures of the compound and at least a singe derivative, or mixtures of derivatives, respectively, which may comprise solvates and/or salts, for instance. It is most preferred to use 2-Methyl-4,5-di-(methylsulfonyl)-benzoyl-guanidine hydrochloride hydrate.

Furthermore, the pharmaceutically usable derivatives may include pro-drug derivatives, i.e. modified compounds having supplemental alkyl groups, acyl groups, sugar molecules or oligo peptides, which are immediately cleaved into the active inventive compound 2-Methyl-4,5-di-(methylsulfonyl)-benzoyl-guanidine within the organism. Herein, biologically degradable polymer derivates of the compound according to the invention are also included as e.g. described in Int. J. Pharm. 115, 61-67 (1995). The compound of the invention can be obtained by liberating it from their functional derivatives by solvolysis, in particular hydrolysis, or by hydrogenolysis.

The active ingredient according to the invention can also be fused or complexed with another molecule that promotes the directed transport to the destination, the incorporation and/or distribution within the target cells.

Furthermore, the active ingredient may be administered alone or in combination with other treatments. A synergistic effect may be achieved by using more than one compound in the pharmaceutical composition, i.e. the compound 2-Methyl-4,5-di-(methylsulfonyl)-benzoyl-guanidine is combined with at least another agent as active ingredient, such as glitazone, exenatide, pramlintide or TZDs. The compounds can be used either simultaneously or sequentially.

The pharmaceutical composition of the invention can be employed as medicament in human and veterinary medicine. It is particularly preferred that the diseases, which are associated with IR and/or ß-cell dysfunction, are represented by T2DM, the Metabolic syndrome, nephropathy and/or neuropathy.

In a preferred embodiment of the invention, the disease underlying the invention is T2DM. The medical indication "T2DM" is a progressive disease which involves the development of IR and other metabolic abnormalities, long before overt glucose intolerance and fasting hyperglycemia are exhibited.

The medical indication "Metabolic syndrome" is a combination of medical disorders that increase the risk of developing cardiovascular diseases. In addition to central obesity, two further symptoms and features have to be fulfilled for classification as the Metabolic syndrome: fasting hyperglycemia (expressed by Type II diabetes mellitus, impaired fasting glucose, impaired glucose tolerance or insulin resistance), high blood pressure and lipometabolic disorder (e.g. decreased HDL cholesterol and/or elevated triglycerides).

The medical indication "nephropathy" relates to diseases of the kidney and kidney function, which are mainly caused non-inflammatorily. The challenging subtype in the scope of the invention is reflected by diabetic nephropathy (nephropatia diabetica), which is also known as Kimmelstiel-Wilson syndrome and intercapillary glomerulonephritis. It is a progressive kidney disease caused by angiopathy of capillaries in the kidney glomeruli, and characterized by nephrotic syndrome and nodular glomerulosclerosis. It is due to long-standing diabetes mellitus, and is a prime cause for dialysis in many Western countries.

The medical indication "neuropathy" is usually short for peripheral neuropathy. Peripheral neuropathy is defined as deranged function and structure of peripheral motor, sensory, and autonomic neurons, involving either the entire neuron or selected levels. Neuropathies often arise secondarily from other diseases, such as diabetes mellitus, or neurotoxic substances, such as alcohol abuse.

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with 2-Methyl-4,5-di-(methylsulfonyl)-benzoyl-guanidine, or derivatives thereof. Examples of suitable excipients are water, vegetable oils, benzyl alcohols, alkylene glycols, polyethylene glycols, glycerol triacetate, gelatin, carbohydrates, such as lactose or starch, magnesium stearate, talc, and petroleum jelly.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

The active ingredients of the instant composition are adapted in forms which are suitable for oral administration, such as tablets, film tablets, coated tablets, lozenges, capsules, pills, powders, granules, syrups, juices, drops, solutions, dispersions, suspensions or depot forms thereof; for transdermal administration, such as solutions, suspensions, creams, ointments, powders, gels, emulsions or band-aids; for parental administration, such as suppositories, suspensions, emulsions, implants or solutions, preferably oily or aqueous solutions; for rectal administration, such as suppositories in particular; for topical application, such as ointments, creams, pastes, lotions, gels, sprays, foams, aerosols, solutions (for example solutions in alcohols, such as ethanol or isopropanol, acetonitrile, DMF, dimethylacetamide, 1,2-propanediol or mixtures thereof with one other and/or with water) or powders; and for intravenous infusion, subcutaneous injection or intramuscular administration, examples for the latter three are solutions and suspensions. The active ingredients can also be adapted for transmucosal, transurethal, vaginal or pulmonary administration in the appropriate formulations given above.

In a preferred embodiment of the present invention, the pharmaceutical composition is orally or parenterally administered, more preferably orally. In particular, the active ingredient is provided in a water-soluble form, such as a pharmaceutically acceptable salt, which is meant to include both acid and base addition salts. The composition may also include one or more of the following: carrier proteins, such as serum albumin, buffers, stabilizing agents, coloring agents, and the like. Additives are well known in the art, and they are used in a variety of formulations.

Furthermore, the 2-Methyl-4,5-di-(methylsulfonyl)-benzoyl-guanidine and derivatives thereof, may be lyophilized and the resulting lyophilizates used, for example, to produce preparations for injection. The basic principles for obtaining lyophilizates are known to the skilled artisan. A method for the production of lyophilizates with improved dilution rate is exemplarily described in DE 199 03 275 A1, which is incorporated as reference in the disclosure of the invention hereby.

The preparations indicated may be sterilized and/or may comprise auxiliaries, such as lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins.

The concentration of the prophylactically or therapeutically active ingredient in the formulation may vary from about 0.1 to 100 wt %. Preferably, the compound 2-Methyl-4,5-di-(methylsulfonyl)-benzoyl-guanidine or the derivatives thereof are administered in doses of approximately 1 to 600 mg, more preferably between 5 and 100 mg per dose unit. Generally, such a dose range is appropriate for total daily incorporation. In other terms, the daily dose is between 0.02 and 200 mg/kg of body weight, preferably between 20 and 100 mg/kg of body weight, more preferably between approximately 0.02 and 10 mg/kg of body weight. The specific dose for each patient depends, however, on a wide variety of factors as already described in the present specification.

The invention also relates to the use of 2-Methyl-4,5-di-(methylsulfonyl)-benzoyl-guanidine, and/or a physiologically acceptable salt and/or solvate thereof, for the production of a medicament for the prophylactic or therapeutic treatment and/or monitoring of diseases that are associated with insulin resistance and/or ß-cell dysfunction. 2-Methyl-4,5-di-(methylsulfonyl)-benzoyl-guanidine, and/or a physiologically acceptable salt and/or solvate thereof, can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The medicament can be used to prevent the initiation of diseases associated with insulin resistance and/or ß-cell dysfunction in advance or to treat the arising and continuing symptoms. The diseases as concerned by the invention are preferably T2DM and/or related diseases thereof, the latter are more preferably selected from the group of the Metabolic syndrome, diabetic nephropathy and neuropathy. The prior teaching of the present specification concerning the pharmaceutical composition is valid and applicable without restrictions to the use of 2-Methyl-4,5-di-(methylsulfonyl)-benzoyl-guanidine and its derivatives for the production of a medicament for prophylaxis and therapy of said diseases.

The aforementioned medical products of the inventive use are particularly used for the therapeutic treatment. Monitoring is considered as a kind of treatment provided that the compound is administered in distinct intervals, e.g. in order to booster the response and eradicate the symptoms of the disease completely. Either the identical compound or different compounds can be applied. In the meaning of the invention, prophylactic treatment is advisable if the subject possesses any preconditions for the onset of T2DM, such as a familial disposition, a genetic defect, or a previously passed disease.

Object of the present invention is also the use of 2-Methyl-4,5-di-(methylsulfonyl)-benzoyl-guanidine, and/ or a physiologically acceptable salt and/or solvate thereof, for the enhancement of insulin sensitivity and/or the preservation or increase of ß-cell compensation. Herein, preservation refers to a similar value within a normal statistical range that is caused by the measurement method and the fact of a living organism involved. A standard deviation of maximal 10% shall be regarded as preservation, preferably maximal 3% only. Contrary to that, the insulin sensitivity will strongly exceed initial values. The insulin sensitivity is at least doubled, preferably at least tripled, more preferably at least quadrupled, and most preferably at least quintupled.

The use according to the previous paragraph of the specification may be either performed in-vitro or in-vivo models. Their ß-cells are either susceptible to deterioration themselves, i.e. they naturally loss function or undergo apoptosis, respectively, or exposed to age-promoting substances, such as pro-apoptotic substances. Similarly, somatic cells can be either insulin resistant themselves, i.e. normal amounts of insulin are inadequate to produce a normal insulin response, or exposed to IR-promoting drugs, such as cortisone, TNF-alpha, PAI-1 or resistin. Both, the aging processes, which are prevented, and the insulin response, which is sensitized, can be monitored by the techniques described in the course of the present specification. The in-vitro use is preferably applied to samples of humans suffering from T2DM. Testing of several specific derivatives of the compound 2-Methyl-4,5-di-(methylsulfonyl)-benzoyl-guanidine makes the selection of that active ingredient possible that is best suited for the treatment of the human subject. The in-vivo dose rate of the chosen derivative is advantageously pre-adjusted to the deterioration susceptibility and/or severity of IR of the respective specific cells with regard to the in-vitro data. Therefore, the therapeutic efficacy is remarkably enhanced. Moreover, the prior teaching of the present specification concerning the use of 2-Methyl-4,5-di-(methylsulfonyl)-benzoyl-guanidine and its derivatives for the production of a medicament for the prophylactic or therapeutic treatment and/or monitoring is considered as valid and applicable without restrictions to the use of the compound for the prevention of reduced ß-cell compensation and increase of IR if expedient.

It is another object of the invention to provide a method for treating Type II diabetes mellitus, the Metabolic syndrome, nephropathy and/or neuropathy, wherein an effective amount of 2-Methyl-4,5-di-(methylsulfonyl)-benzoyl-guanidine, and/or a physiologically acceptable salt and/or solvate thereof, is administered to a mammal in need of such treatment. The mammals to be treated are humans in particular. The preferred treatment is an oral or parenteral administration. The treatment of the patients with T2DM or people bearing a risk of developing T2DM on the basis of existing IR by means of the NHE1-inhibitor 2-Methyl-4,5-di-(methylsulfonyl)-benzoyl-guanidine improves the whole-body insulin sensitivity and ameliorates IR in these individuals. The prior teaching of the invention and its embodiments is valid and applicable without restrictions to the method of treatment if expedient.

In the scope of the present invention, 2-Methyl-4,5-di-(methylsulfonyl)-benzoyl-guanidine is used for the prophylactic or therapeutic treatment and/or monitoring of human diseases that are associated with insulin resistance and/or ß-cell dysfunction for the first time. The invention addresses the role of ß-cell compensation in response to prolonged insulin resistance. The aforementioned effects are interrelated such that 2-Methyl-4,5-di-(methylsulfonyl)-benzoyl-guanidine acts either as a peripheral insulin sensitizer (secondarily preserving β-cell function by reducing the secretory burden on the pancreas) or as a direct insulin secretagogue (secondarily improving insulin sensitivity by increasing tissue insulinization), or both. As result of providing the pharmaceutical composition according to the invention, the insulin sensitivity is increased while the age-related decrease in ß-cell function (compensation) is prevented, but may even be reversed. Its use is a promising, novel approach for a broad spectrum of therapies causing a direct and immediate reduction of symptoms. The impact is of special benefit to efficiently combat T2DM and illnesses arising from T2DM. The compound and derivatives thereof are characterized by a high specificity and stability; low manufacturing costs and convenient handling. These features form the basis for a reproducible action, wherein the lack of cross-reactivity and adverse effects is included, and for a reliable and safe interaction with their matching target structures.

It is to be understood that this invention is not limited to the particular pharmaceutical composition, use and method described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "an active ingredient" includes a single or several different active ingredients, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used.

BRIEF DESCRIPTION OF THE DRAWINGS

FIG. 13a shows the concentration at successive time points in response to a glucose challenge. FIG. 13b shows the area under curve (AUC 60 min) for glucose response graphed in FIG. 13a. FIG. 13c shows the concentration at successive time points in response to a glucose challenge. FIG. 13d shows the AUC 60 min insulin response graphed in FIG. 13c. For FIGS. 13b and 13d the different groups are represented by the bars from left to right: Lean Veh, fa/fa-Veh, Cmp A 40 mpk, Cmp A 80 mpk, Cmp B 40 mpk, Cmp 80 mpk.

FIG. 14a shows the concentration of glucose at successive time points in response to glucose challenge. FIG. 14b shows the area under curve (AUC 60 min) for glucose response graphed in FIG. 14a. FIG. 14c shows the concentration of insulin at successive time points in response to a glucose challenge. FIG. 14d shows the AUC 60 min of the insulin response graphed in FIG. 14c. For FIGS. 14b and 14d the different groups are represented by the bars from left to right: Lean Veh, fa/fa-Veh, Cmp A 40 mpk, Cmp A 80 mpk, Cmp B 40 mpk, Cmp 80 mpk.

FIG. 15a shows the concentration of glucose in response to a glucose challenge. FIG. 15b shows the area under curve (AUC 60 min) for glucose response graphed in FIG. 15a. FIG. 15c the concentration of insulin at successive time points in response to a glucose challenge. FIG. 15d shows the AUC 60 min for insulin response graphed in FIG. 15c. For FIGS. 15b and 15d the different groups are represented by the bars from left to right: Lean Veh, fa/fa-Veh, Cmp A 40 mpk, Cmp A 80 mpk, Cmp B 40 mpk, Cmp 80 mpk.

PHARMACOLOGICAL STUDY REPORT I

Study Design

Figure 1:
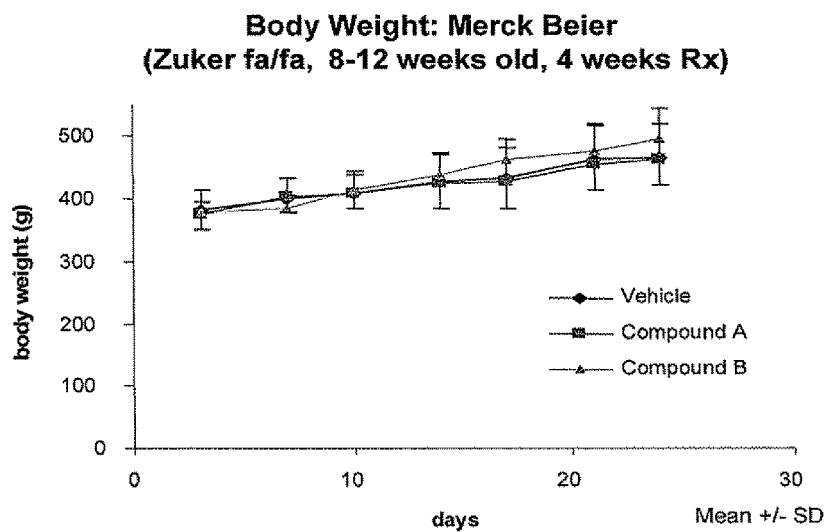
FIG. 1 shows the body weight of ZF (fa/fa) rats at the age of 8-12 week during treatment (Mean+/−SD, n=12).

Obese, insulin resistant ZF (fa/fa) rats, which are treated from the age of 8-12 weeks, were used as IR model. Rats were housed with a 12-h light/dark cycle and free access to food and water unless otherwise noted. Studies were approved by the Institutional Animal Care and Use Committee. There were a total of 18 animals in the study (8 week-old males, provided by Charles River). Animals were randomized into 3 groups (vehicle group, Compound A group, Compound B group, n=6 per group) based on random glucose level at the beginning of the study:

Group 1: ZF rats (fa/fa) (n=6), compound A (150 mg/kg via gavage)

Group 2: ZF rats (fa/fa) (n=6), compound B (40 mg/kg/day as admixture to the chow)

Group 3: ZF rats (fa/fa) (n=6), vehicle treatment (control chow, vehicle gavage)

Group 1 and 3 animals were treated with compound A or vehicle (water) for 4 weeks (from age 8-12 weeks) via oral gavage, twice daily. Chow containing compound B was fed to Group 2 ad lib. Group 1 and Group 3 were fed with chow without compound B ad lib.

Compound A corresponds to Cariporide. Compound B corresponds to 2-Methyl-4,5-di-(methylsulfonyl)-benzoyl-guanidine hydrochloride hydrate.

Blood Sampling and Plasma Glucose and Insulin Assays

Random morning blood was withdrawn from ad libitium fed rats by a small cut in the tip of the tail. Blood was collected in heparinized tubes. Blood glucose concentrations were measured as per study design using a One-Touch glucometer (Lifescan Inc, Milptias, Calif.). Blood samples were placed on ice and centrifuged, and plasma stored at −20° C. until insulin was assayed. Rat plasma insulin concentration was measured with rat-specific ELISA kit (Crystal Chem Inc, Downers Grove, Ill.).

$^2$H-GDT

Rats underwent a 4 hour fast. One hour prior to the $^2$H-GDT challenge rats received 1.75 mg/g of body weight of $H_2O^{18}$ (10% $^{18}$O, Spectra, X XX) by oral gavage to allow the determination of total body water as previously described. At t=0, the blood glucose concentrations were determined with a glucometer, and a blood sample was obtained for determination of base line insulin and $H_2O^{18}$ dilution. Animals then received [6,6'-$^2$H]glucose (2 g/kg body weight, 50% in water, Cambridge Isotope Laboratory, Inc., Andover, Mass.) by oral gavage. The 2 g/kg oral glucose load used in the rat protocol achieved glucose levels within or near the desired dynamic range. A second blood sample was collected at t=30 min for determination of glucose and insulin concentrations and $^2H_2O$ content.

Heavy Water Labeling Protocol

Animals received an IP bolus (0.35 µl/g body weight) of 99% heavy water in 0.9% NaCl to reach a body water enrichment of roughly 5% (using an estimated 60% body weight as water) and then received 8% $^2H_2O$ in drinking water for last 4 weeks of study. Body water $^2H_2O$ enrichments reach stable steady-state values within a few days in rodents on this protocol.

IRMS Analysis

One hundred micro liter aliquots of plasma samples inside the cape of an inverted vial were placed in a heating blocked filled with glass beads at 70° C. overnight and the water distillate inside the vial was collected. The deuterium and oxygen-18 isotope ratios of the blood of plasma samples were determined using a Thermo Finnigan High Temperature Conversion/Elemental Analyzer coupled with a Thermo Finnigan MAT 253 IRMS via a Conflo-III Interface. The first two measurements were discarded to minimize hysteresis effects from the previous sample. The deuterium isotope abundance is first calculated in δ 2H values relative to the international VSMOW standard, and then transformed to APE by using a calibration curve of standards with known enrichments. The $^2H_2O$ enrichment was calculated for rats at 30 min after the glucose load. $^2H_2O$ enrichment was converted to mmoles by multiplying enrichment by the TBW pool size and dividing by 20 (MW $^2H_2O$). Total $^2H_2O$ produced was calculated as a percent of the [6,6'-$^2H_2$] glucose load given. Plasma insulin (INS AUC) and glucose (GLU AUC) areas under the curves were calculated using the trapezoidal method. Two $^2$H-GDT parameters were calculated: 1)$^2H_2O$ production (% load)/INS AUC*GLU AUC and 2) the absolute rate of $^2H_2O$ production (% load).

Results

Body Weight

There were no significant differences in body weight (FIG. 1) among the vehicle-, Compound A- or Compound B-treated groups.

Random Morning Blood Glucose Level

Figure 2:
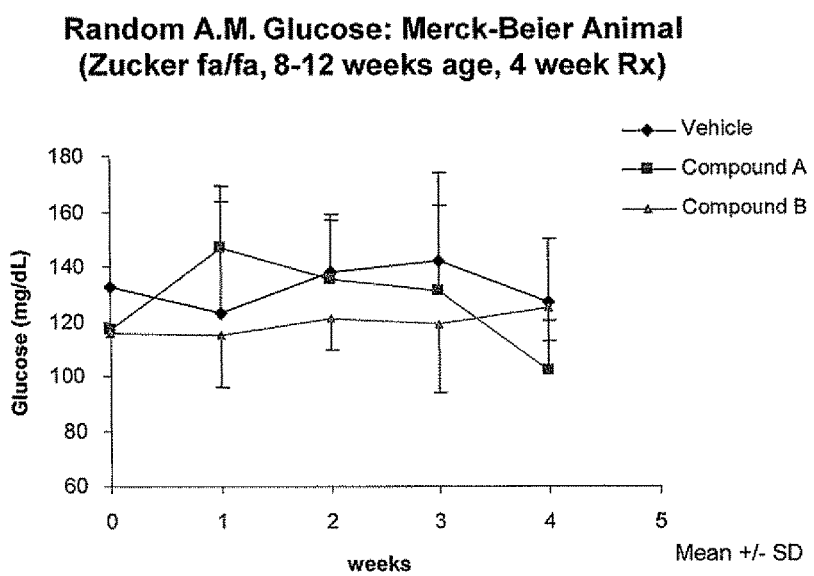
FIG. 2 shows the random morning glucose level of ZF (fa/fa) rats at the age of 8-12 week during treatment (Mean+/−SD, n=12, *p<0.05). Week 4 data are 4 hour fasted glucose readings from GDT group.

Random morning blood glucose levels were measured weekly between 9-11 a.m. There was no significant difference in random morning blood glucose levels between Compound B-treated and vehicle groups during the 4 weeks of this study (FIG. 2). However, Compound A-treated group trended towards lower glucose level by the end of the study compared to the other two groups.

Fasting Glucose and Insulin Levels

Figure 3:
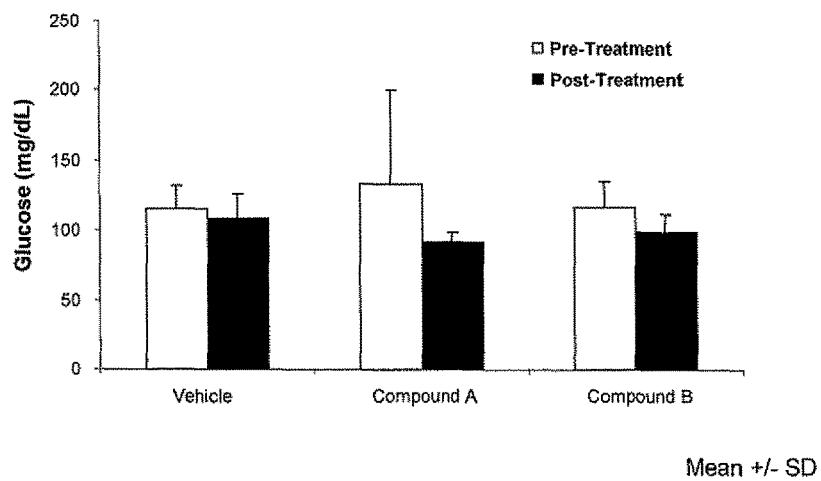
FIG. 3 shows the fasting blood glucose level in ZF (fa/fa) rats at the age of 12 weeks following 4 weeks of treatment (Mean+/−SD, n=6).
Figure 4:
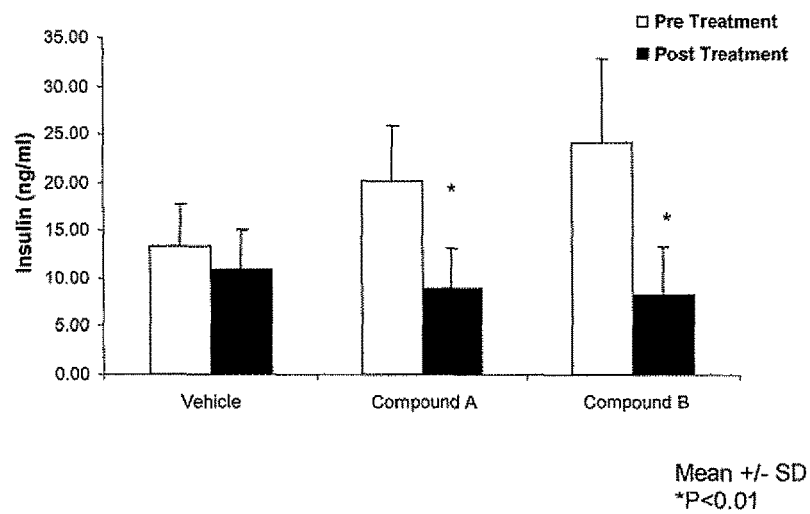
FIG. 4 shows the fasting insulin level in ZF (fa/fa) rats at the age of 12 weeks following 4 weeks of treatment (Mean+/−SD, n=6, *p<0.01).

At the end of the study, rats were fasted for 4 hours and glucose and insulin level were measured. Fasting glucose levels in Compound A- and Compound B-treated animals trended towards lower values post treatment, while there were no significant differences in the vehicle treated group, pre- and post-treatment (FIG. 3). There were significantly lower fasting insulin levels in both compound A- and Compound B-treated animals compared to their pre-treatment levels (FIG. 4).

GDT

All animals underwent $^2$H-GDT both prior and following the 4 weeks treatment. For the $^2$H-GDT, animals were fasted for 4 hours. One hour prior to the $^2$H-GDT challenge, the rats received 1.75 mg/g body weight of $H_2^{18}O$ by oral gavage to allow the determination of total water content. At t=0 min, a blood sample was obtained for the determination of base line insulin, glucose and $H_2^{18}O$ dilution. Then, [6,6'-$^2H_2$] glucose (2 g/kg body weight, 50% in water) was administered to the animals by oral gavage. Serial blood samples were taken for glucose and insulin concentrations and $^2H_2O$ content at 90 min time point. The adequacy of pancreatic compensation was assessed by distinguishing between the absolute rate of glucose utilization achieved (reflecting pancreatic compensation to IR) and the glycolytic disposal of administered glucose per unit of ambient insulin (reflecting insulin sensitivity). The β-cell compensation is expressed as the % $^2H_2O$ recovery after the oral [6,6'-$^2H_2$] glucose load and the insulin sensitivity is expressed as the % $^2H_2O$ recovery per insulin AUC.

Figure 5:
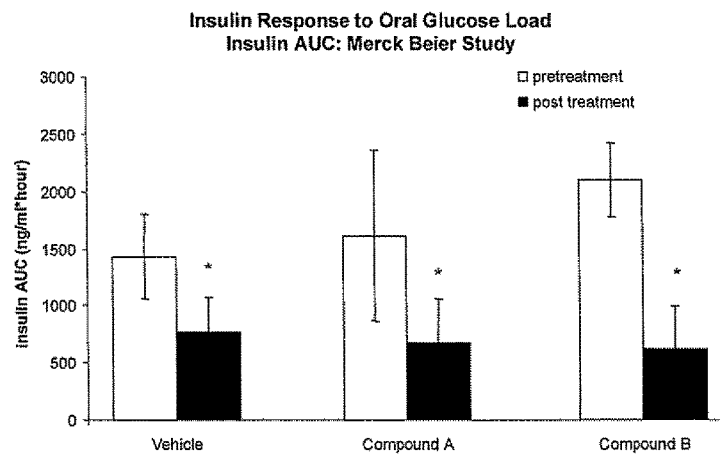
FIG. 5 shows the insulin responses (insulin AUC) to an oral glucose load in ZF (fa/fa) rats at the age of 12 weeks following 4 weeks of treatment (Mean+/−SD, n=6, GDT, *p<0.01 vs. pre-treatment).
Figure 6:
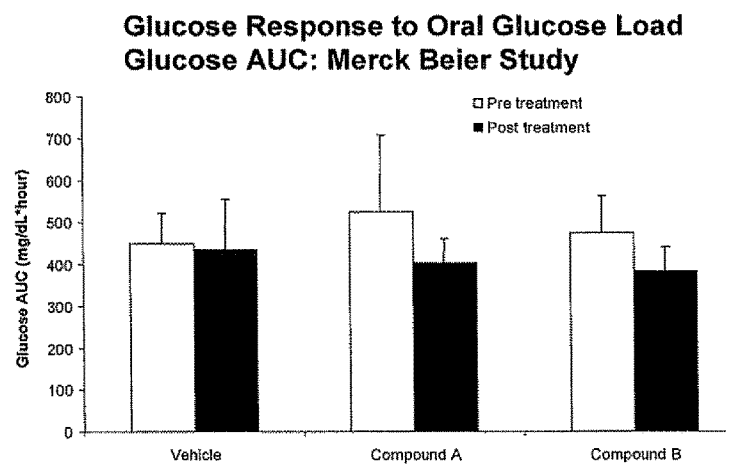
FIG. 6 shows the glucose response (glucose AUC) to an oral glucose load in ZF (fa/fa) rats at the age of 12 weeks following 4 weeks of treatment (Mean+/−SD, n=6, CDT).

There were no significant differences in insulin AUC (FIG. 5) or glucose AUC levels (FIG. 6) among the three groups either pre- or post-treatment. Glucose AUC during the oral glucose load followed a similar trend as fasting glucose levels. As can be seen, there was a large standard deviation, likely representing physiologic variation. However, all post-treatment insulin AUC levels were significantly lower compared to pre-treatment. The fall in vehicle-treated animals likely represents the natural history of ß-cell deterioration with aging (from age of 8 to 12 weeks) in ZF rats.

Figure 7:
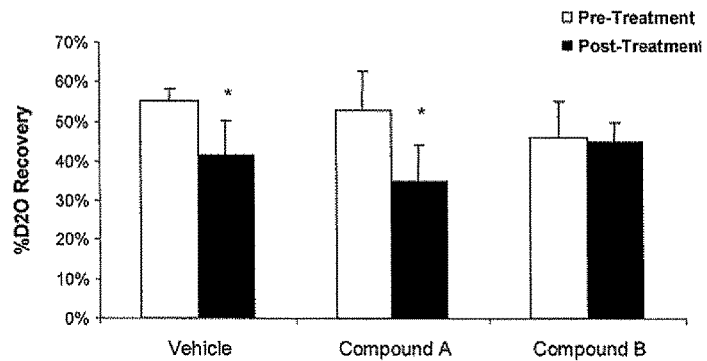
FIG. 7 shows the pancreatic compensation as quantified by deuterated glucose disposal test ($^2$H-GDT; 90 minute % $D_2O$ recovery) in ZF (fa/fa) rats at the age of 12 weeks following 4 weeks of treatment (Mean+/−SD, n=6, GDT group, *p<0.01).

Since the change of insulin AUC in Compound A- and Compound B-treated animals may be either caused by age-related deterioration or reduced insulin needs due to improved insulin sensitivity, the reason was figured out by GDT measurement. There were no significant differences among groups in pancreatic compensation, both pre- and post-treatment. Comparisons of compensation before and after treatment within each group, however, revealed that both vehicle and compound A groups exhibited lower pancreatic compensation post-treatment (FIG. 7), most likely due to the natural progression of ß-cell dysfunction in ZF rats. In contrast, Compound B-treated ZF rats maintained the same degree of pancreatic compensation as was present at baseline. These results suggest preservation of ß-cell function in response to Compound B treatment only.

Figure 8:
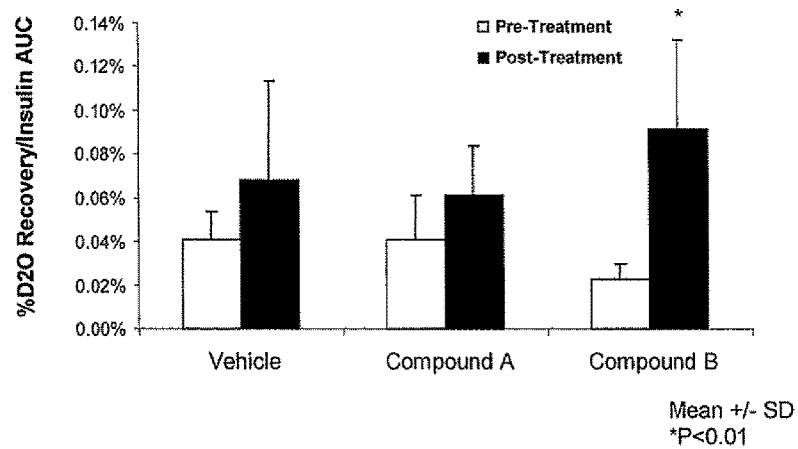
FIG. 8 shows the insulin sensitivity as quantified by deuterated glucose disposal test ($^2$H-GDT; % $D_2O$ recovery/ insulin AUC) in ZF (fa/fa) rats at the age of 12 weeks following 4 weeks of treatment (Mean+/−SD, n=6, *p<0.01).

Consistent with these findings, insulin sensitivity measured by the GDT (FIG. 8) showed that Compound B-treated animals had significantly increased insulin sensitivity (~4 fold) compared to pre-treatment values while there was no significant change in insulin sensitivity post-treatment in the vehicle- and Compound A-treated groups compared to pre-treatment, although there was a trend toward increased values in both groups. Thus, 2-Methyl-4,5-di-(methylsulfonyl)-benzoyl-guanidine hydrochloride hydrate as represented by Compound B significantly increased insulin sensitivity and prevented the age-related reduction in ß-cell compensation, indicating that the reduction in insulin AUC post-treatment was physiologic in Compound B-treated animals. These results also emphasized the need to characterize insulin sensitivity when assessing insulin concentrations in models of insulin resistance.

PHARMACOLOGICAL STUDY REPORT II

Study Design

In the previous $^2$H-GDT study (Pharmacological Study Report I), Compound B increased insulin sensitivity (SI) and either increased or maintained the β-cell responsiveness (pancreatic compensation) in Zucker fa/fa rats. However in this study, the baseline fasting insulin levels differed between groups. There was an overall reduction in fasting insulin levels and the insulin AUC in all groups of animals, despite the fact that there were no changes in random glucose, fasting glucose, or the glucose AUC in any of the treatment groups. The objective of the present study was to confirm the original observations of the effects of compounds A and B on SI and pancreatic compensation (PC). A secondary objective was to better define the time course of the drugs' effects on the glucose and insulin responses to an oral glucose load. A number of changes were made from the previous study:
1. Compounds A and B were mixed with food to eliminate the stress of daily oral gavage. The presence of drug in the diet did not adversely affect food intake and would give an acceptable concentration of drug in the plasma.
2. Zucker fa/fa rats were assigned to a treatment group on the basis of preliminary measurements of body weight, fasting glucose and insulin concentrations, and glycosylated hemoglobin A1c levels (Gly-HbA1c), to eliminate potential bias in the final results.
3. Fasting glucose and insulin concentrations were determined weekly.
4. $^2$H-GDT was carried out on Days 0, 14 and 28. In addition, during the $^2$H-GDT, blood glucose and insulin levels were determined at 0, 15, 30, 60 and 90 min to better define both the insulin and glucose responses.
5. Glycosylated HbA1c levels were determined on Days 0 and 28 to provide an additional assessment of any overall improvement in glucose homeostasis achieved by treatment.
6. A lean control group was included in the study.

Subjects

Thirty-six obese Zucker fa/fa and six lean Zucker fa/? male rats obtained from Charles River, were housed under normal vivarium conditions on a 12 hour light/dark cycle. The rats were kept two to a cage with food and water available ad lib, except during the weekly, 4 hour fasts. Water continued to be available during these fasts.

Drug

Compound A corresponds to Cariporide. Compound B corresponds to 2-Methyl-4,5-di-(methylsulfonyl)-benzoyl-guanidine hydrochloride hydrate. Compounds A and B were supplied in powder form by Merck Serono. Drugs were incorporated into a pelleted diet (LabDiet, 5001) by Research Diets, Inc (New Brunswick, N.J.) at concentrations of 0.44 g/kg or 0.88 g/kg of diet to yield approximate doses of 40 or 80 mg/kg. The concentration was calculated based on the assumption that a 300 g rat would eat about 30 g/d of chow. The same chow, but without drug, was fed to rats of both the lean and fa/fa control group animals.

Group Assignment

One week prior to the start of the study, all rats were weighed. After a 4 hour fast, a blood sample was obtained for the determination of blood glucose, insulin, and glycosylated hemoglobin levels (HbA1c). Animals were then sorted on the basis of these parameters into the groups listed below. Rats were eight weeks of age at the onset of treatment.

Treatment Groups:
1. ZF rats (fa/fa) (n=6) chow without drug
2. ZF rats (fa/fa) (n=6) compound A (40 mg/kg/day)
3. ZF rats (fa/fa) (n=6) compound A (80 mg/kg/day)
4. ZF rats (fa/fa) (n=6) compound B (40 mg/kg/day)
5. ZF rats (fa/fa) (n=6) compound B (80 mg/kg/day)
6. lean Zucker rats (fa/?) (n=6) chow without drug Dosing Regime Treatment appropriate chow was continuously available for 4 weeks except during scheduled 4 h fasts conducted once per week.

Body Weight and Food Intake individual body weights were determined once per week. Average food intake per cage was also determined once per week and the individual rat consumption was calculated by dividing the cage average by 2 (rats housed 2/cage).

Glucose and Insulin Levels

Both random and fasting (4 h) blood glucose levels were determined using a hand-held glucometer (OneTouch Ultra, Lifescan, Inc. Milapitas, Calif.) on blood obtained from tail capillary samples. Plasma insulin levels were determined by a rat specific ELISA (Ultra Sensitive Rat Insulin ELISA Kit, Crystal Chem, Inc., Chicago, Ill.). The 4 h fast period started at 9 a.m. and ended after a blood draw at 1 p.m.

HbA1c Levels

HbA1c level were determined using a DCA 2000 analyzer (Bayer Healthcare LLC, Elkhart Ind.) prior to beginning the study and again at the end of the $4^{th}$ week treatment period.

$^2$H-GDT

Insulin sensitivity (SI) and pancreatic compensation (PC) were measured by conducting $^2$H-Glucose disposal test on Days 0, 14 and 28.

Time −4 h: Before the fast was begun on the morning of the GDT, a blood sample was taken to determine the random glucose level (see above). An additional blood sample was collected to determine the baseline $^2$H$_2$O and $^{18}$O enrichments. The rats were weighed and the 4 h fast was begun. Water was available during the fast.

Time −3 h: One 1 hour after the start of the fast, 1.75 mg/g body weight of 10% H$_2$$^{18}$O was administered by oral gavage ($^2$H$_2$O-free H$_2$O$^{18}$ water; 10% $^{18}$O atom from Spectra; Cat. No 51350).

Time 0: 4 hours after the start of the fast, the blood glucose and insulin levels were determined. Rats received 4 ml/kg of a 50% glucose solution (comprised of 25% [6,6-$^2$H$_2$] glucose and 25% D-glucose) by oral gavage.

At times 15, 30, 60 and 90 min post glucose challenge, blood glucose concentrations were again determined by a glucometer reading from tail vein blood. Additional blood samples were collected for insulin determinations. At 60 and 90 min post glucose challenge, whole blood was collected to determine the $^2$H$_2$O and H$_2$$^{18}$O enrichments. All blood samples were centrifuged and the plasma was stored at −20° C. until assayed. The deuterium and oxygen-18 isotope enrichments of body water were determined by IRIS analysis of the water distillate of the plasma samples.

Calculations $^2$H$_2$O enrichment was converted to mmol by multiplying enrichment ($^2$H$_2$O APE) by the total body water pool size and dividing by 20 (molecular weight of $^2$H$_2$O). Total $^2$H$_2$O produced was calculated as the percent of the [6,6-$^2$H$_2$] glucose load administered. Plasma insulin and glucose areas under the curve (AUC 60 min) were calculated using the trapezoidal method (GraphPad Prism).

Two parameters were calculated from the $^2$H-GDT:
1. Insulin sensitivity index (SI)=$^2$H$_2$O production (% load)/(glucose AUC×insulin AUC).

2. Pancreatic compensation (PC)=the absolute $^2H_2O$ production as a percent of total [6,6-$^2H_2$] glucose load (% load)/the integrated glucose response (glucose AUC; to correct for insulin-independent utilization).

Statistics

Overall results of glucose and insulin measures were analyzed by a 2 way repeated measures ANOVA using drug and time (repeated) as factors. The primary analysis was followed by Bonferroni posttests to compare all groups. Data are considered significant at p<0.05. AUC 60 min values for glucose and insulin were analyzed by 1 way ANOVA followed by Tukey's comparison of all groups.

Data Exclusion

Data that indicated that there was a lack of enrichment due to a failure, or partial failure of glucose administration during the $^2$H-GDT, were omitted.

Results

Pre-Study Group Assignment

There were no significant differences between fa/fa groups at the start of the study. As expected, the lean animals' body weight and fasting insulin levels differed significantly from all fa/fa animals. Although the glycosylated hemoglobin and fasting glucose levels were somewhat lower in lean animals, these values were not significantly different from those of other treatment groups (Table 1).

TABLE 1

Pre-study body weights, fasting blood glucose, insulin and Gly-HbA1c levels. Data are the Means ± SEM, n = 6/group; *p < 0.001, differs significantly compared to all fa/fa treatment groups.

| Group | Lean fa/? Chow | fa/fa chow | fa/fa cmp A 40 mg/kg | fa/fa cmp A 80 mg/kg | fa/fa cmp B 40 mg/kg | fa/fa cmp B 80 mg/kg |
|---|---|---|---|---|---|---|
| BW (g) | 259.6 ± 2.7* | 378.9 ± 12.6 | 381.2 ± 15.3 | 377.2 ± 12.6 | 379.1 ± 13.0 | 376.3 ± 11.6 |
| BG (mg/dl) | 100.6 ± 2.6 | 113.6 ± 6.0 | 113.2 ± 6.4 | 118.7 ± 10.3 | 109.5 ± 6.7 | 122.8 ± 6.4 |
| Insulin (ng/ml) | 1.0 ± 0.2* | 10.5 ± 1.4 | 10.3 ± 1.0 | 10.8 ± 1.7 | 11.1 ± 0.8 | 10.3 ± 0.6 |
| HbA1c (%) | 3.5 ± 0.1 | 3.8 ± 0.1 | 4.0 ± 0.2 | 3.9 ± 0.1 | 3.8 ± 0.1 | 4.0 ± 0.1 |

Body Weight and Food Intake

Figure 9:
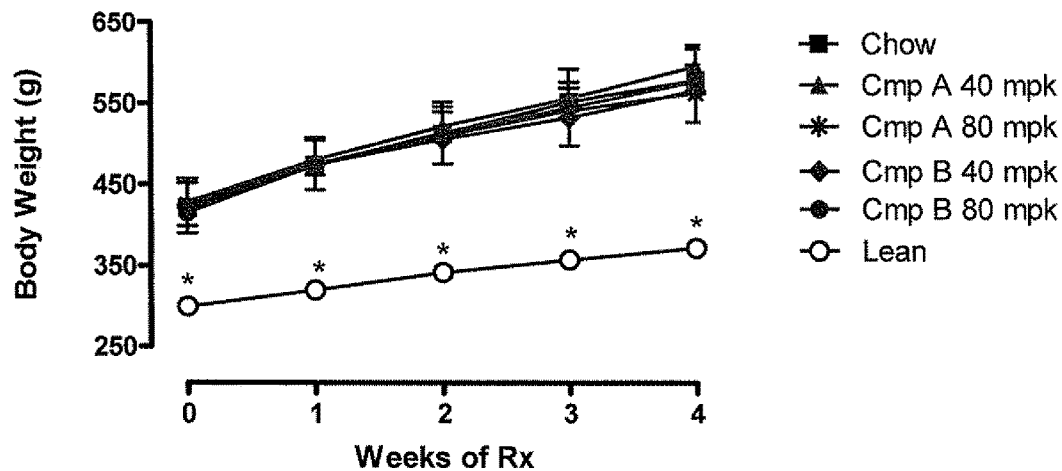
FIG. 9 shows the body weights of Zucker fa/fa and lean control rats during drug treatment period. Data are the average+/−standard deviation; n=6/group (error bars are obscured by symbols); *p<0.01 from control fa/fa rats.

All animals continued to gain weight for the duration of the experiment, indicating that the drugs were well tolerated (2 way repeated measure ANOVA followed by Bonferroni posttests: time: $F_{(4,136)}$=1488.41, p<0.0001; treatment: $F_{(6,36)}$=31.02, p<0.0001, interaction treatment x time: $F_{(24,138)}$=12.69, p<0.0001). No significant difference in body weight was noted between the fa/fa groups over the 4 week treatment period (FIG. 9), although all were increased relative to the lean control group. The average weekly food intake of the Compound A and Compound B groups was increased compared to lean controls, but did not differ significantly from that of chow fed fa/fa controls (Table 2).

TABLE 2

Average food consumption in grams during the 4 week treatment period. Data are the average +/− standard deviation; *p < 0.01 from chow fa/fa control.

| Treatment | Week 1 | Week 2 | Week 3 | Week 4 |
|---|---|---|---|---|
| Chow fa/fa control | 34.1 +/− 2.0 | 32.7 +/− 5.6 | 34.7 +/− 1.5 | 35.3 +/− 1.9 |
| Compd A 40 mg/kg | 32.2 +/− 3.5 | 33.1 +/− 2.6 | 33.9 +/− 2.4 | 34.9 +/− 2.7 |
| Compd A 80 mg/kg | 34.3 +/− 2.5 | 32.8 +/− 4.3 | 32.3 +/− 4.5 | 30.8 +/− 5.6 |
| Compd B 40 mg/kg | 32.1 +/− 3.2 | 33.8 +/− 2.9 | 31.7 +/− 2.9 | 33.6 +/− 4.4 |
| Compd B 80 mg/kg | 31.8 +/− 1.4 | 32.9 +/− 1.9 | 33.0 +/− 0.7 | 34.0 +/− 2.9 |
| Lean control | 21.2 +/− 1.5* | 22.0 +/− 1.3* | 21.1 +/− 0.8* | 21.8 +/− 0.9* |

Random Blood Glucose

Figure 10:
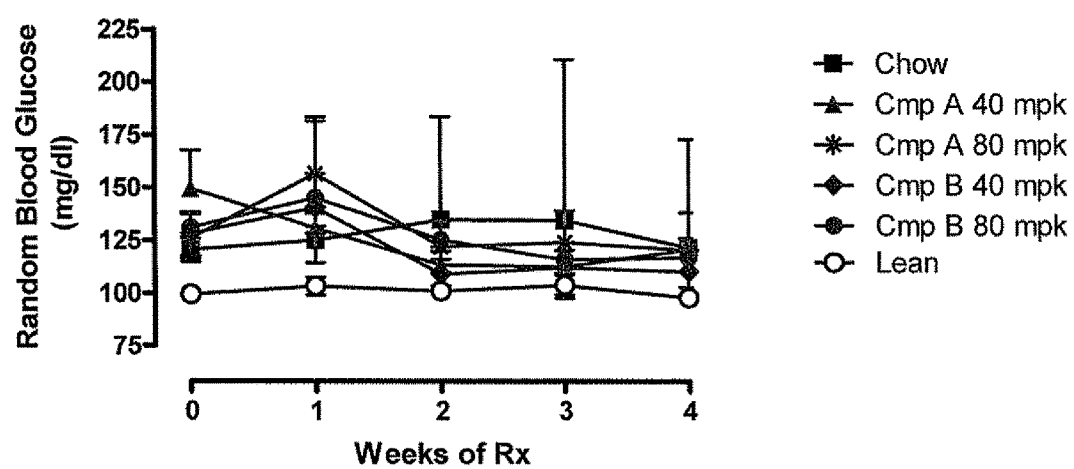
FIG. 10 shows the random blood glucose determined once per week at approximately 9 a.m. There were no significant differences between groups. Data are the average+/−standard deviation; n=6/group.

Random blood glucose was determined once per week at approximately 9 a.m. in non-fasted rats. There was no significant difference between the random glucose levels of the chow fa/fa group and any of the other treatment groups (FIG. 10) (2 way repeated measure ANOVA followed by Bonferroni posttests: treatment $F_{6,136}$=0.93; p=0.48 ns; time: $F_{4,136}$=3.25, p=0.01; interaction $F_{24,136}$=0.97, p=0.51 ns).

Fasting Blood Glucose Levels

Figure 11:
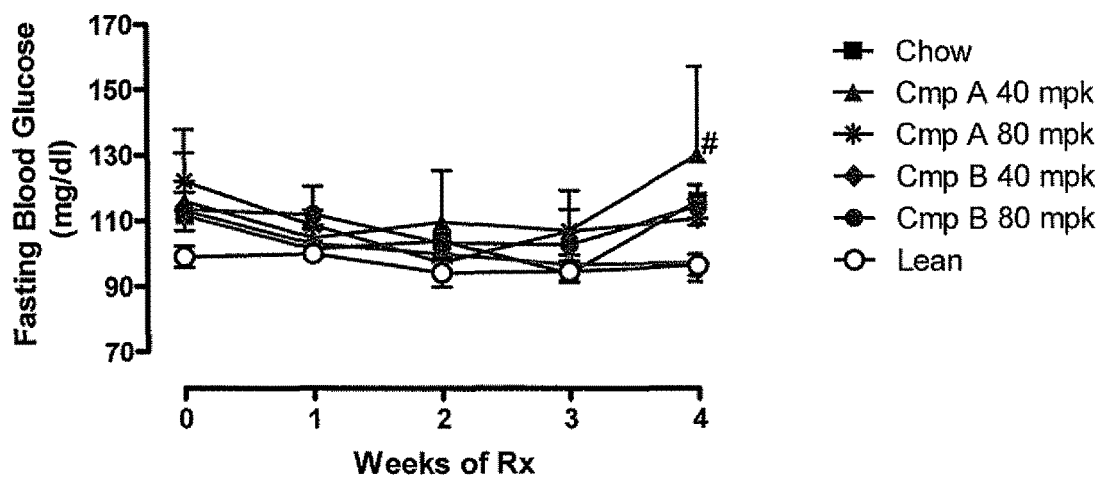
FIG. 11 shows the 4 h fasting blood glucose concentrations as determined by a glucometer reading during 4 weeks of drug treatment. Data are the average+/−standard deviation; n=6/group; # different than lean control (Bonferroni posttest).

Fasting blood glucose was determined once per week after a 4 h fast (fast at 9 a.m., sample at 1 p.m.). Glucose levels in the various drug treatment groups did not differ significantly from the control fa/fa group (FIG. 11). The 40 mg/kg dose of Compound A increased the fasting glucose concentration after 4 weeks of administration (2 way repeated measure ANOVA followed by Bonferroni posttests: treatment: $F_{6,136}$=5.26; p=0.0006; time: $F_{4,136}$=7.68, p=0.0001; interaction $F_{24,136}$=0.97, p=0.51 ns).

Fasting Insulin Concentrations

Figure 12:
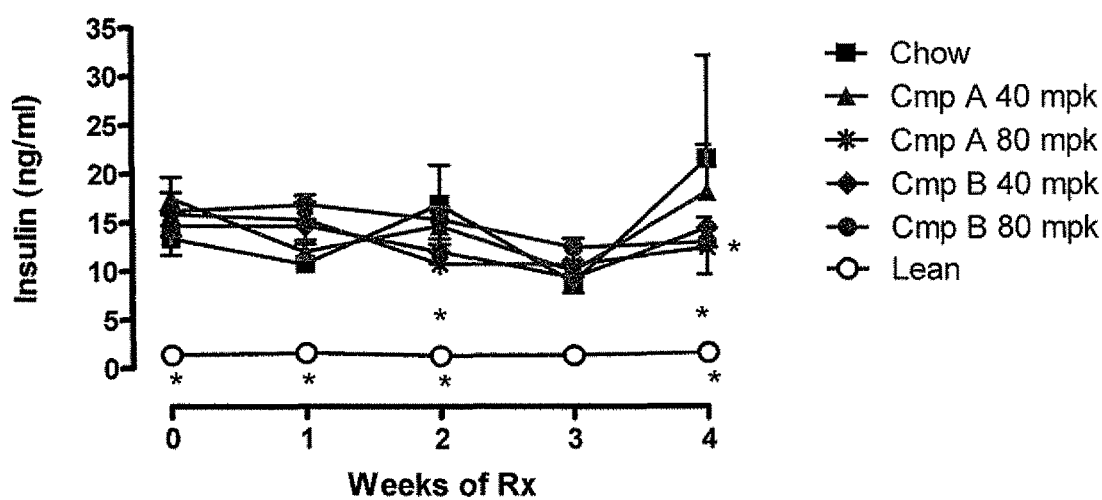
FIG. 12 shows the insulin concentrations after a 4 hour fast determined at one week intervals. Data are the average+/−standard deviation; n=6/group; * significantly different than fa/fa chow (vehicle) control.

Fasting insulin concentrations at baseline and after 4 weeks of treatment are summarized in Table 3 (2 way repeated measure ANOVA followed by Bonferroni posttests: treatment: $F_{6,36}$=11.24, p<0.0001; time: $F_{6,36}$=9.48, p<0.0001; interaction: $F_{24,136}$=3.21, p<0.0001). The insulin concentrations of the lean controls were significantly different from those of the chow fed fa/fa control at each week, with the exception of the $3^{rd}$ week. By the $4^{th}$ week of treatment both Compound A at 80 mg/kg significantly decreased fasting insulin relative to the fa/fa vehicle control. These values, however, remained higher than those of the lean controls (FIG. 12).

Glycosylated Hemoglobin

HbA1c levels reflect glycemic control over time. At baseline, the mean HbA1c levels of all fa/fa groups were somewhat, but not significantly, higher than that of lean controls. At week 4, the HbA1c levels of the fa/fa control group and the Compound B 80 mg/kg group were significantly higher than those of the lean controls (Table 3). The changes in HbA1c were not statistically significant between any of the treatment groups over the 4 week treatment period (Table 3).

Pancreatic Function and Insulin Sensitivity
Pretreatment

Insulin sensitivity and pancreatic compensation determined at baseline were similar in all fa/fa groups (FIG. 16a, b) and were significantly reduced compared to lean controls. This indicates the ability of fa/fa rats to compensate to their severe insulin resistance is incomplete and contributes to

TABLE 3

Baseline, Week 4 and the change over the 4 week treatment period of fasting insulin and HbA1c. Data are the Means ± SD, n = 5-6/group; *significantly different than fa/fa vehicle (chow) control; #significantly different than lean control (Tukey test, p < 0.05).

| Group | Lean fa/? Chow | Fa/fa chow | fa/fa cmp A 40 mg/kg | fa/fa cmp A 80 mg/kg | fa/fa cmp B 40 mg/kg | fa/fa cmp B 80 mg/kg |
|---|---|---|---|---|---|---|
| Baseline Insulin (ng/ml) | 1.4 ± 0.5* | 13.4 ± 2.9# | 17.6 ± 5.1# | 15.9 ± 5.5# | 14.7 ± 2.7# | 16.2 ± 11.2# |
| Week 4 Insulin (ng/ml) | 1.7 ± 0.5* | 21.6 ± 10.7# | 18.2 ± 11.8# | 12.5 ± 7.5*# | 14.5 ± 5.5# | 13.1 ± 8.2# |
| Change in Insulin (ng/ml) | 0.3 ± 0.8 | 8.2 ± 9 | 0.6 ± 9.6 | −3.4 ± 8.2 | −0.2 ± 4.4 | −3.2 ± 11.2 |
| Base line HbA1c (%) | 3.5 ± 0.1 | 3.8 ± 0.4 | 4.0 ± 0.5 | 3.9 ± 0.4 | 3.8 ± 0.2 | 4.0 ± 0.4 |
| Week 4 HbA1c (%) | 3.8 ± 0.1* | 4.7 ± 0.7# | 4.4 ± 0.2 | 4.4 ± 0.52 | 4.3 ± 0.3 | 4.8 ± 0.4# |
| Change in HbA1c (%) | 0.4 ± 0.2 | 0.9 ± 0.4 | 0.4 ± 0.6 | 0.4 ± 0.9 | 0.4 ± 0.2 | 0.8 ± 0.7 |

$^2$H-Glucose Disposal Test

Figure 13:
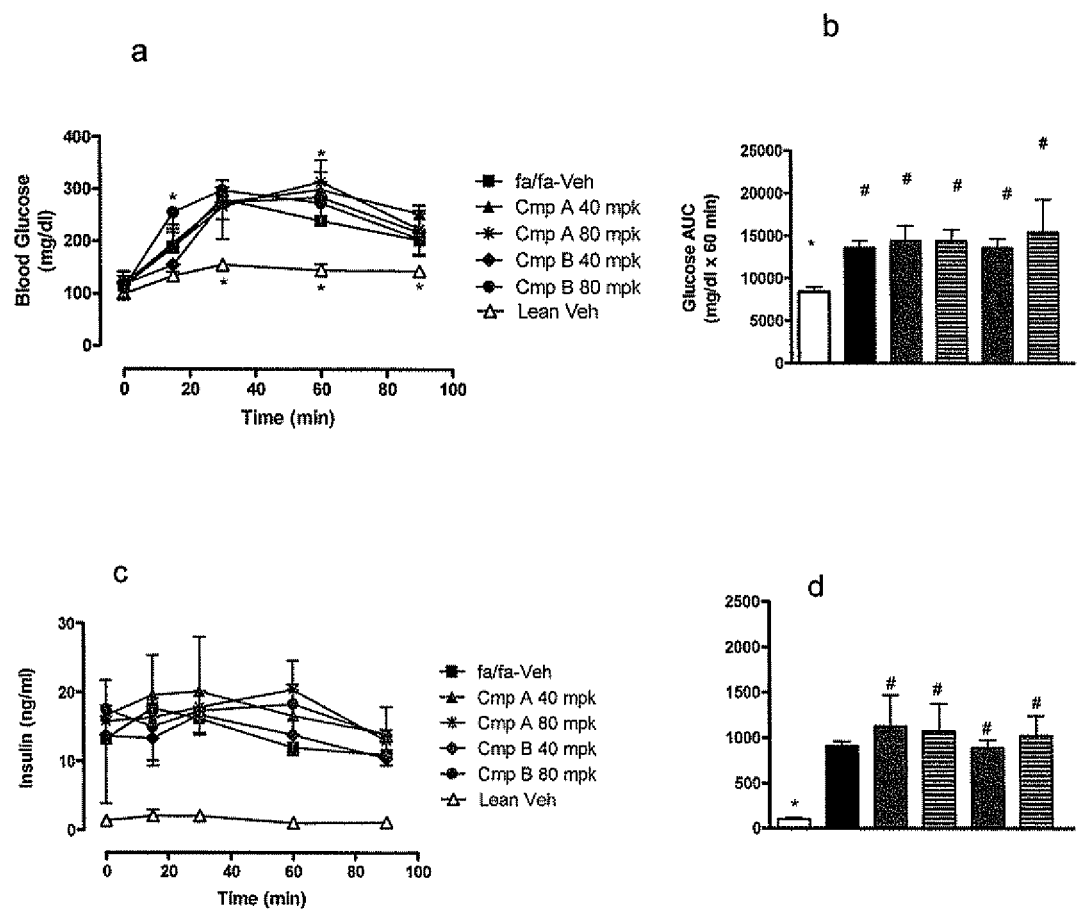
FIG. 13 relates to pretreatment and shows the blood glucose and insulin concentrations in response to a glucose challenge during the GDT prior to starting drug treatment. Data are the average+/−standard deviation (error bars are obscured by symbol for some groups); n 6 for Compound A 80 mg/kg and lean control; n=5 for fa/fa veh, Compound A 40 mg/kg, Compound B 40 mg/kg; n=4 for Compound B 80 mg/kg; * different than fa/fa vehicle control; # significantly different than lean vehicle.

To determine the effect of compounds A and B on pancreatic function and insulin sensitivity, rats underwent a $^2$H-GDT prior to animals being weaned onto chow with drug, and then after 2 and 4 weeks of drug treatment Pretreatment $^2$H-GDT Glucose and Insulin Response In response to a glucose challenge before the start of drug treatment, blood glucose concentrations were increased in all fa/fa rats relative to the lean controls (FIG. 13a). At the 60 min time point, the glucose levels of both the 40 and 80 mg/kg Compound A to-be-assigned groups were increased above those of the fa/fa vehicle to-be-assigned animals. However, the glucose AUC (60 min) indicated that all groups of fa/fa rats had a similar degree of impaired oral glucose tolerance relative to the lean controls (FIG. 13b). At baseline, all fa/fa animals displayed a similar degree of impaired hyperinsulinemia compared to the lean controls during the $^2$H-GDT challenge (FIG. 13c, d).

Figure 14:
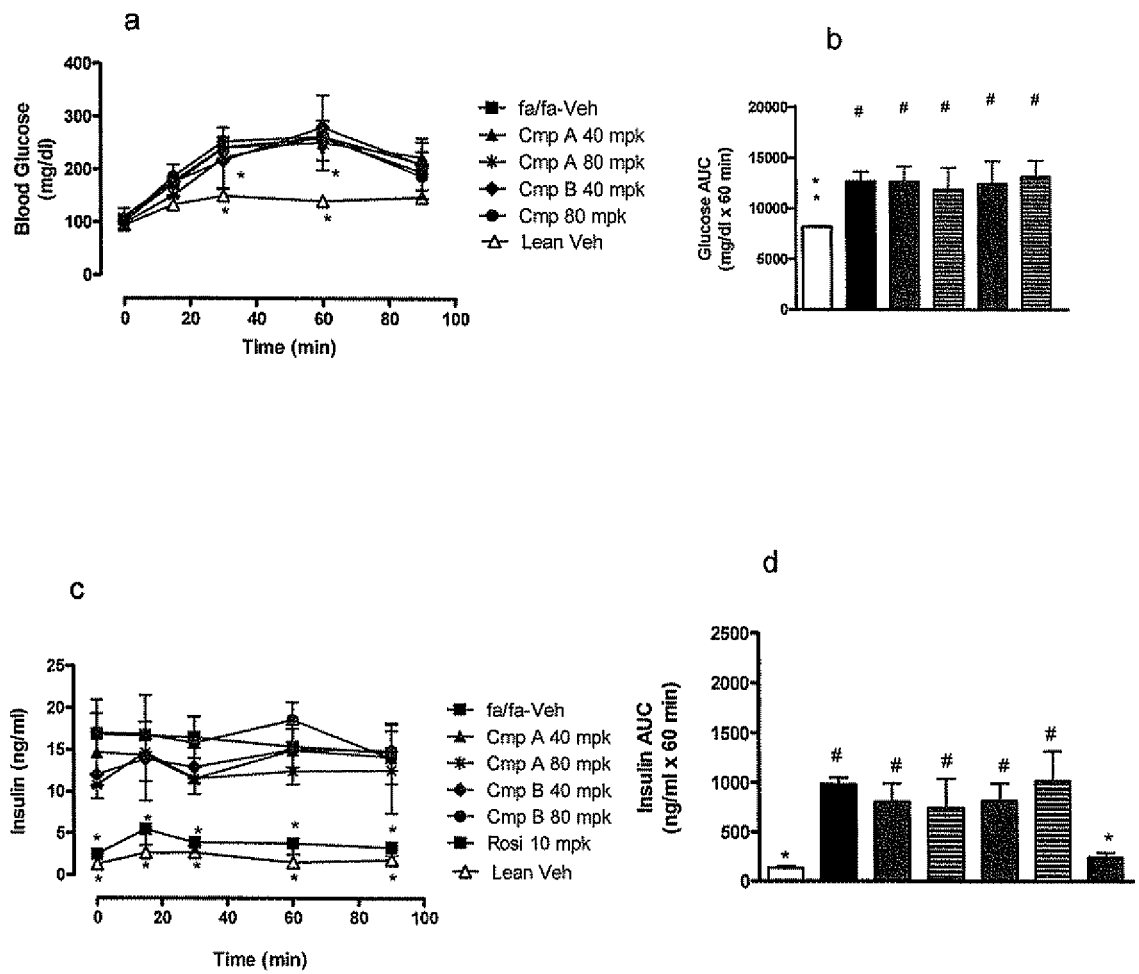
FIG. 14 relates to 2 weeks of drug treatment and shows the blood glucose and insulin concentrations in response to a glucose challenge during the GDT 2 weeks after starting drug treatment. Data are the average+/−standard deviation (error bars are obscured by symbol some groups); n=6 for fa/fa veh, Compound A 40 mg/kg, Compound A 80 mg/kg, Compound B 40 mg/kg and lean control; n=4 for Compound B 80 mg/kg; * different than fa/fa chow vehicle; # significantly different than lean vehicle.

Two Week $^2$H-GDT Glucose and Insulin Response 2 weeks after the start of drug treatment, all fa/fa animals had a significant increase in blood glucose concentrations relative to the lean controls (FIG. 14a, b). Likewise all fa/fa animals had increased insulin concentrations relative to the lean controls (FIG. 14c, d). Compounds A and B did not affect the glucose or insulin response after 2 weeks of treatment.

Figure 15:
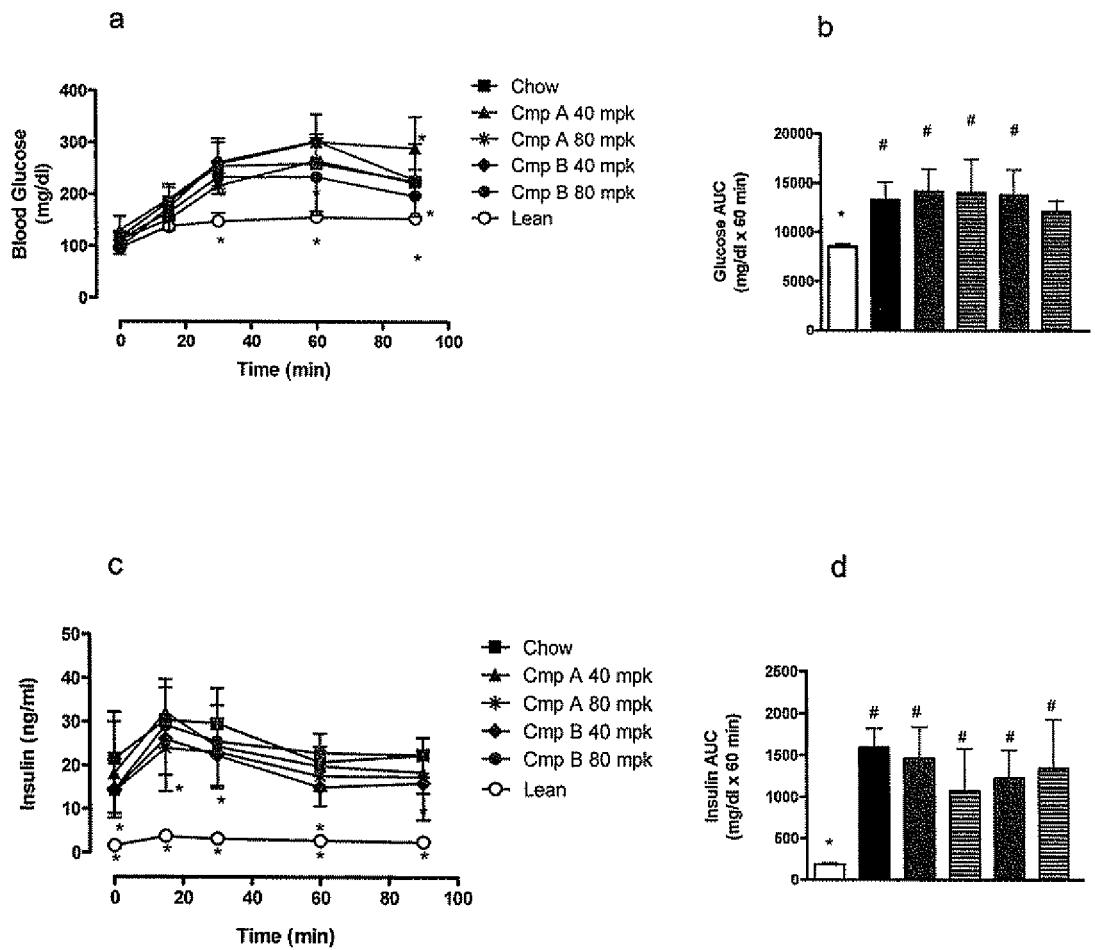
FIG. 15 relates to 4 weeks of drug treatment and shows the blood glucose and insulin concentration in response to a glucose challenge during the $3^{rd}$ GDT that occurred 4 weeks after starting drug treatment. Data are the average+/−standard deviation (error bars are obscured by symbols in some cases); n=6 for fa/fa chow, Compound A 40 mg/kg, Compound B 40 mg/kg and lean control; n=5 for Compound A 80 mg/kg, Compound B 80 mg/kg; * different than fa/fa chow vehicle; # different than lean control.

Four Weeks GDT Glucose and Insulin Response 4 weeks after the start of drug treatment, rats dosed with compound A (40 and 80 mg/kg) and compound B (40 and 80 mg/kg) continued to have elevated blood glucose and insulin concentrations (FIG. 15a, b, c, d). In fact at the 90 min time point, the glucose level was elevated above that of the fa/fa vehicle treated rats in the Compound A 40 mg/kg treated group. At 80 mg/kg, Compound B slightly decreased blood glucose levels such that the values were not significantly different from those of the lean vehicle rats or the fa/fa vehicle controls. Insulin concentrations remained elevated in the 80 mg/kg Compound B group.

their glucose intolerance. The apparent reduction in pancreatic compensation observed in the group of animals that were later treated with 80 mg/kg of Compound B may be considered to be an experimental artifact since this decrease was not observed at later time points and these animals did not differ on other measures made at the same time (e.g. weight, fasting glucose or insulin concentrations). Results of ANOVA for PC: $F_{6,29}$=33.02, p<0.0001; for SI: $F_{6,29}$=35.8, p<0.0001.

Two Weeks of Treatment

Figure 16:
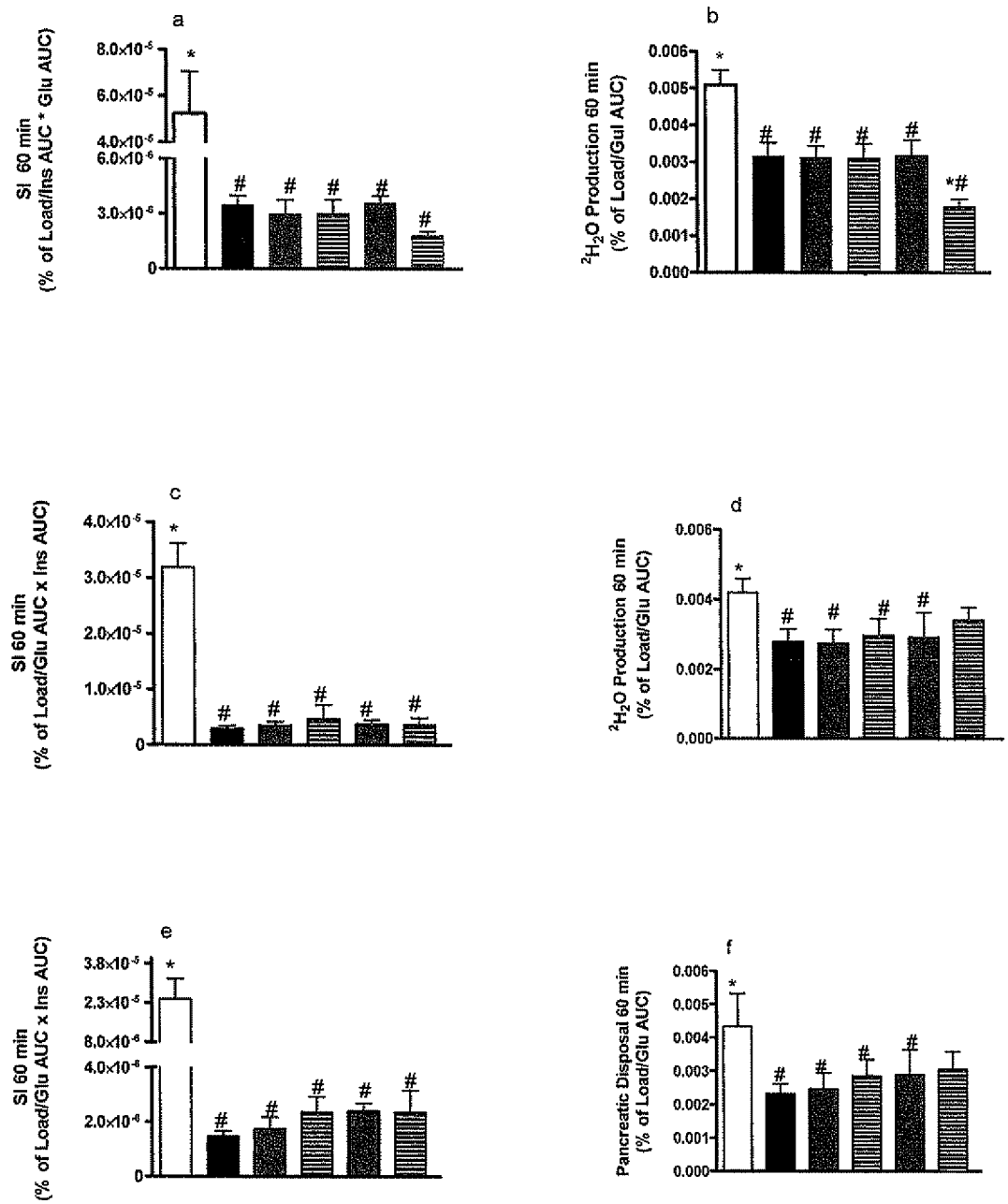
FIG. 16 shows the insulin sensitivity (a, c, e) and pancreatic compensation (b, d, e) in response to a glucose challenge pretreatment (a, b), 2 weeks after start of treatment (c, d) and 4 weeks after start of treatment (e, f). * significantly different than vehicle treated (chow) fa/fa; # significantly different than lean control (ANOVA followed by Tukey test). For FIGS. 16a-16f the different groups are represented by the bars from left to right: Lean Veh, fa/fa-Veh, Cmp A 40 mpk, Cmp A 80 mpk, Cmp B 40 mpk, Cmp 80 mpk.

After 2 weeks of treatment, pancreatic compensation in the Compound B, 80 mg/kg group was intermediate between that of the lean and fa/fa control groups (FIG. 16c, d). Results of ANOVA for PC: $F_{6,32}$=9.121, p<0.0001; for SI $F_{6,32}$=132.7, p<0.0001.

Four Weeks of Treatment

After 4 weeks of drug treatment, the results were similar to those of 2 weeks (FIG. 16e, f). Although insulin sensitivity in the 80 mg/kg Compound B group was not significantly improved, there was a slight improvement in pancreatic compensation. Results of ANOVA for PC: $F_{6,32}$=6.17, p=0.0002; for SI: $F_{6,32}$=35.01, p<0.0001.

Conclusions

At baseline, there were no significant differences between the fa/fa groups in body weight, food consumption, HbA1c, random blood glucose, fasting blood glucose or insulin concentrations. Likewise, in response to a glucose challenge, fa/fa groups did not differ from one another in the glucose AUC (60 min) or insulin AUC (60 min), but were significantly different than the lean controls. Both insulin sensitivity and pancreatic compensation were similar in all fa/fa rats at baseline, with the exception of the Compound B (80 mg/kg/d) group which was depressed relative to the other groups. After 4 weeks of treatment, 80 mg/kg of Compound A decreased fasting insulin concentrations, but was without effect on any of the other parameters. Neither dose of Compound A significantly improved glucose levels (either fasting or in response to challenge), insulin sensitivity or pancreatic compensation. The effects of Compound B in the present experiments were moderate. After 4 weeks of treatment at 80 mg/kg/d, Compound B decreased glucose AUC 60 min in response to a glucose challenge. The glucose concentration was intermediate between that of the lean and fa/fa vehicle controls, but slightly different from either. There was practically no effect on the insulin AUC 60 min, or on the computed measure of insulin sensitivity (SI). Pancreatic compensation appeared to be slightly improved after both 2 and 4 weeks of treatment and was slightly different from either the lean or the fa/fa vehicle controls. It is noted, however, that pancreatic compensation in this group appeared to be lower (worse) than that of the other groups at baseline. 4 weeks of treatment with Compound A did not improve glucose tolerance or significantly improve the hyperinsulinemia and exaggerated insulin responses observed in fa/fa rats. The high dose of Compound B attenuated the deterioration in pancreatic compensation relative to the fa/fa controls. Compound B has a positive effect on pancreatic function, even though it does not effectively increase insulin sensitivity.

EXAMPLES RELATED TO PHARMACEUTICAL PREPARATIONS

Example A: Injection Vials

A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, lyophilized under sterile conditions and sealed under sterile conditions. Each injection vial contains 5 mg of active ingredient.

Example B: Suppositories

A mixture of 20 g of an active ingredient according to the invention is melted with 100 g of soya lecithin and 1400 g of cocoa butter, poured into moulds and allowed to cool. Each suppository contains 20 mg of active ingredient.

Example C: Solution

A solution is prepared from 1 g of an active ingredient according to the invention, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilized by irradiation. This solution can be used in the form of eye drops.

Example D: Ointment 500 mg of an active ingredient according to the invention are mixed with 99.5 g of Vaseline under aseptic conditions.

Example E: Tablets

A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

Example F: Coated Tablets

Tablets are pressed analogously to Example E and subsequently coated in a conventional manner with a coating of sucrose, potato starch, talc, tragacanth and dye.

Example G: Capsules 2 kg of an active ingredient according to the invention are introduced into hard gelatin capsules in a conventional manner in such a way that each capsule contains 20 mg of the active ingredient.

Example H: Ampoules

A solution of 1 kg of an active ingredient according to the invention in 60 l of bidistilled water is sterile filtered, transferred into ampoules, lyophilized under sterile conditions and sealed under sterile conditions. Each ampoule contains 10 mg of active ingredient.

Example I: Inhalation Spray 14 g of an active ingredient according to the invention are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

The invention claimed is:

1. A method for the treatment of the arising symptoms of a disease that is associated with ß-cell dysfunction having reduced ß-cell compensation, comprising administering to a patient who has not progressed to type II diabetes an effective amount of an active ingredient which is 2-methyl-4,5-di-(methylsulfonyl)-benzoyl-guanidine, and/or a physiologically acceptable salt and/or solvate thereof, such that the ß-cell dysfunction in the patient is decreased, wherein the 2-methyl-4,5-di-(methylsulfonyl)-benzoyl-guanidine and/or a physiologically acceptable salt and/or solvate thereof acts as direct insulin secretagogue and wherein the pancreatic ß-cell compensation in the patient is preserved to at least 70% of baseline prior to usage.

2. The method of claim 1, wherein the active ingredient is a 2-methyl-4,5-di-(methylsulfonyl)-benzoyl-guanidine salt selected from the hydrochloride, methanesulfonate, hemisulfate, hemi-fumerate and hemi-malate salts.

3. The method of claim 1, wherein the active ingredient is 2-methyl-4,5-di-(methylsulfonyl)-benzoyl-guanidine hydrochloride hydrate.

4. The method of claim 1, wherein the active ingredient is administered by oral or parenteral administration.

5. The method of claim 1, wherein the active ingredient is administered by oral administration.

6. A method according to claim 1, wherein the pancreatic ß-cell compensation in the patient is preserved to at least 80% of baseline prior to usage.

7. A method according to claim 6, wherein the active ingredient is administered for a period of at least 4 weeks.

8. A method for the treatment of ß-cell dysfunction having reduced ß-cell compensation in a patient who has not progressed to type II diabetes, comprising administering to the patient an effective amount of an active ingredient which is 2-methyl-4,5-di-(methylsulfonyl)-benzoyl-guanidine, and/or a physiologically acceptable salt and/or solvate thereof, wherein the 2-methyl-4,5-di-(methylsulfonyl)-benzoyl-guanidine and/or a physiologically acceptable salt and/or solvate thereof acts as direct insulin secretagogue and wherein the pancreatic ß-cell compensation in the patient is preserved to at least 70% of baseline prior to usage.

9. A method according to claim 1, wherein the active ingredient maintains or increases ß-cell response in the patient.

10. A method according to claim 1, wherein the active ingredient is administered to the patient in a dose of 1 to 600 mg per dose unit.

11. A method according to claim 1, wherein the active ingredient is administered to the patient in a dose of 5 to 100 mg per dose unit.

12. A method according to claim 1, wherein the active ingredient is administered to the patient in a daily dose of between 0.02 and 200 mg/kg of patient body weight.

13. A method according to claim 1, wherein the active ingredient is administered to the patient in a daily dose of between 20 and 100 mg/kg of patient body weight.

* * * * *